(12) United States Patent
Kwak et al.

(10) Patent No.: US 9,249,109 B2
(45) Date of Patent: Feb. 2, 2016

(54) METHOD FOR PREPARING DIPEPTIDYL PEPTIDASE-IV INHIBITOR AND INTERMEDIATE

(71) Applicant: DONG-A PHARMACEUTICAL. CO., LTD, Seoul (KR)

(72) Inventors: Woo Young Kwak, Yongin-si (KR); Heung Jae Kim, Seongnam-si (KR); Jong Pil Min, Yongin-si (KR); Tae Hyun Yoon, Yongin-si (KR); Moohi Yoo, Seoul (KR); Geun Gho Lim, Seoul (KR); Sun Ki Chang, Gunpo-si (KR)

(73) Assignee: DONG-A PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 14/506,025

(22) Filed: Oct. 3, 2014

(65) Prior Publication Data

US 2015/0025241 A1 Jan. 22, 2015

Related U.S. Application Data

(62) Division of application No. 13/259,699, filed as application No. PCT/KR2010/001947 on Mar. 30, 2010, now abandoned.

(30) Foreign Application Priority Data

Mar. 30, 2009 (KR) ........................ 10-2009-0027105

(51) Int. Cl.
| | |
|---|---|
| C07C 227/02 | (2006.01) |
| C07D 241/08 | (2006.01) |
| C07C 29/36 | (2006.01) |
| C07C 247/10 | (2006.01) |
| C07C 255/44 | (2006.01) |
| C07C 269/06 | (2006.01) |
| C07C 271/22 | (2006.01) |
| C07D 203/08 | (2006.01) |
| C07D 203/18 | (2006.01) |
| C07C 29/10 | (2006.01) |
| C07C 241/00 | (2006.01) |
| C07C 253/00 | (2006.01) |
| C07C 255/42 | (2006.01) |
| C07D 203/10 | (2006.01) |

(52) U.S. Cl.
CPC ............ *C07D 241/08* (2013.01); *C07C 29/106* (2013.01); *C07C 29/36* (2013.01); *C07C 227/02* (2013.01); *C07C 241/00* (2013.01); *C07C 247/10* (2013.01); *C07C 253/00* (2013.01); *C07C 255/42* (2013.01); *C07C 255/44* (2013.01); *C07C 269/06* (2013.01); *C07C 271/22* (2013.01); *C07D 203/08* (2013.01); *C07D 203/10* (2013.01); *C07D 203/18* (2013.01); *Y02P 20/55* (2015.11)

(58) Field of Classification Search
CPC ............................. C07C 227/02; C07D 241/08
USPC .................... 544/384; 562/443; 548/965, 966
See application file for complete search history.

(56) References Cited

U.S. PATENT DOCUMENTS

2008/0280913 A1   11/2008   Harbeson

FOREIGN PATENT DOCUMENTS

| WO | WO2006/098342 A1 | 9/2006 |
| WO | WO2008/113565 A1 | 9/2008 |
| WO | WO2008/130151 A1 | 10/2008 |

OTHER PUBLICATIONS

Tesfaye Biftu, et al; (3R)-4-[(3R)-3-Amino-4-(2,4,5-trifluorophenyl)butanoyl]-3- . . . ; Bioorganic & Med. Chem. Ltrs.; vol. 17; 2007; pp. 49-52.

Mi Ae Jun, et al; SAR Study of B-Aminoacyl-containing cyclic hydrazide . . . ; Bull. Korean Chem. Soc.; vol. 29; No. 11; 2008; pp. 2129-2134.

Peter G.M. Wuts, et al; Greene's protective groups in organic synthesis, Fourth edition; 2007; Protection for the amino group; pp. 696-926.

*Primary Examiner* — Scarlett Goon
*Assistant Examiner* — Ana Z Muresan
(74) *Attorney, Agent, or Firm* — Lucas & Mercanti, LLP

(57) ABSTRACT

The present invention relates to an improved method for preparing dipeptidyl peptidase-IV inhibitor intermediates. The present invention is able to reduce preparation costs by using low cost reagents on reaction and is able to be used in mass production by improving yield.

5 Claims, No Drawings

US 9,249,109 B2

METHOD FOR PREPARING DIPEPTIDYL PEPTIDASE-IV INHIBITOR AND INTERMEDIATE

CROSS REFERENCE TO RELATED APPLICATIONS

This application is a divisional of U.S. patent application Ser. No. 13/259,699, filed Sep. 23, 2011, which is 371 of PCT/KR2010/001947 filed on Mar. 30, 2010, which claims the benefit of Korean Patent Application No. 10-2009-0027105 filed Mar. 30, 2009, the contents of each of which are incorporated herein by reference.

FIELD OF INVENTION

The present invention relates to an improved method for manufacturing dipeptidyl peptidase-IV inhibitor and an intermediate.

BACKGROUND OF INVENTION

DPP-IV is an enzyme functioned as a cleavage of N-terminal dipeptide of peptide having a terminal sequence of H-Xaa-Pro-Y (or H-Xaa-Ala-Y, where Xaa is any lipophilic amino acid, Pro is proline, and Ala is alanine) (Heins J et al. *Biophys Acta* 1988; 161), and also called DP-IV, DP-4, or DAP-IV. After finding out that DPP-IV degrades glucagon-like protein-1 (hereinafter, called as to GLP-1) that is known to have a powerful effect on a control function of insulin to blood glucose contents after dinner (Mentlein R et al. *Eur J Biochem* 1993:829-35), a possibility as very powerful therapeutic agent for Type II diabetes is presented, and then a study for developing DPP-IV inhibitor has become faster.

Merck Company developed triazolo piperazine compound with beta-amino acid structure, sitagliptin, during an investigation about DPP-IV inhibitor. The compound is the first DPP-IV inhibitor for treating Type II diabetes and has now become commercially available under a trademark, Januvia™, around the world after obtaining the new medicine approval from U.S. FDA in 2006. On this matter, Korean Patent Publication No. 2008-0094604 discloses that when triazolo piperazine part of sitagliptin is substituted with piperazinone containing hetero atom, it has an excellent DPP-IV inhibition activity, and also a significantly improved bioavailability as compared to that of the conventional DPP-IV inhibitor; and provides a heterocyclic compound containing new beta-amino group represented by the following Chemical Formula 1, or pharmaceutically acceptable salt thereof, a method for manufacturing the same, and a pharmaceutical composition, which contains the same as an effective component, for preventing and treating diabetes or obesity.

[Chemical Formula 1]

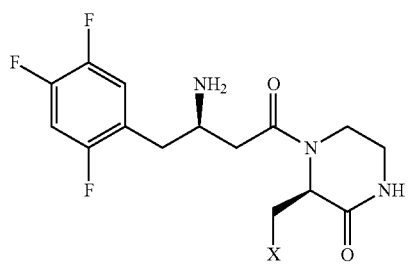

As shown in the following Reaction Formula A, Korean Patent Publication No. 2008-0094604 discloses a method for manufacturing heterocyclic compound represented by Chemical Formula 1 with beta-amino group, the method comprising I) preparing a compound represented by Chemical Formula 4 bonded with peptide bond by reacting a compound with beta-amino group represented by Chemical Formula 2 and a substituted heterocyclic compound represented by Chemical Formula 3 using 1-hydroxybenzotriazol (HOBT), 1-ethyl-3-(3-dimethylaminopropyl)carbodiimide (EDC), and tertiary amine; and II) reacting the compound represented by Chemical Formula 4 under an acid condition:

[Reaction Formula A]

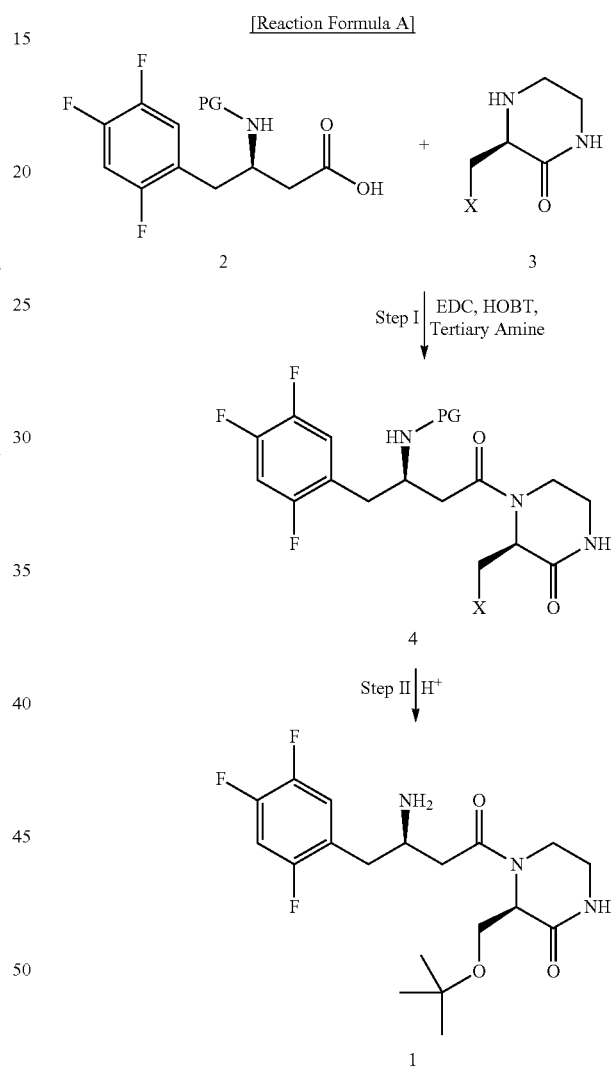

(In the above Reaction Formula A, PG is a protecting group.)

At this time, the compound with beta-amino group represented by Chemical Formula 2 in the above Reaction Formula A may be used for manufacturing various DPP-IV inhibitors as disclosed in International Laying-Open Gazettes WO03/000181, WO03/004498, WO03/082817, WO04/007468, WO04/032836, WO05/011581, WO06/097175, WO07/077,508, WO07/063,928, WO08/028,662, WO08/087,560, and the like, besides the production of DPP-IV inhibitor represented by the above Chemical Formula 1, and may be produced through various methods.

For example, the compound represented by the above Chemical Formula 2 may be produced by using the method as disclosed in *J. Med. Chem.* 2005; 141 and Synthesis 1997; 873 as shown in the following Reaction Formula:

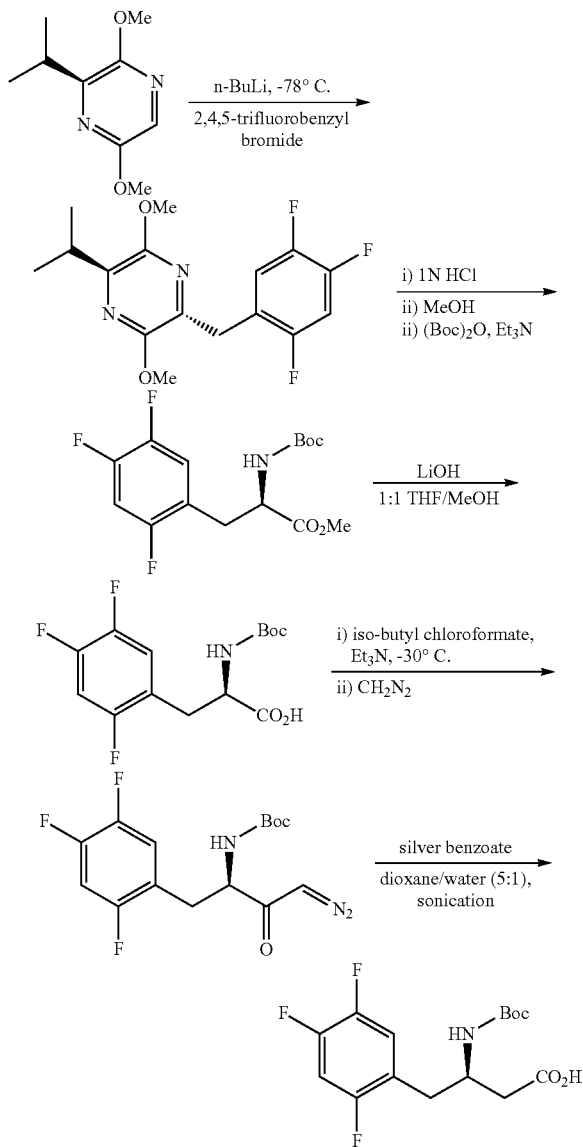

Specifically, ester compound is obtained through an amine-protecting reaction after reacting (2S)-(+)-2,5-dihydro-3,6-dimethoxy-2-isopropylpirazine with 2,4,5-trifluorobenzyl bromide and acid-treating. The ester compound may be again hydrolyzed to obtain 3-(2,4,5-trifluorophenyl)-2-aminopropionic acid; then diazoketone may be formed by using isobutyl chloroformate, tertiary amine such as triethyl amine or diisopropylethyl amine, and diazomethane; and the compound represented by Chemical Formula 2 may be produced by reacting the diazoketone with silver benzoate. However, the reaction as mentioned above has problems that it should be performed at low temperature (−78° C.), or should use an expensive alpha-amino acid and highly risky diazomethane.

Other method for manufacturing the compound represented by the above Chemical Formula 2 is also known in *Tetrahedron: Asymmetry* 2006; 205 or similarly *Bioorganic & Medicinal Chemistry Letters* 2007; 2622, as shown in the following Reaction Formula:

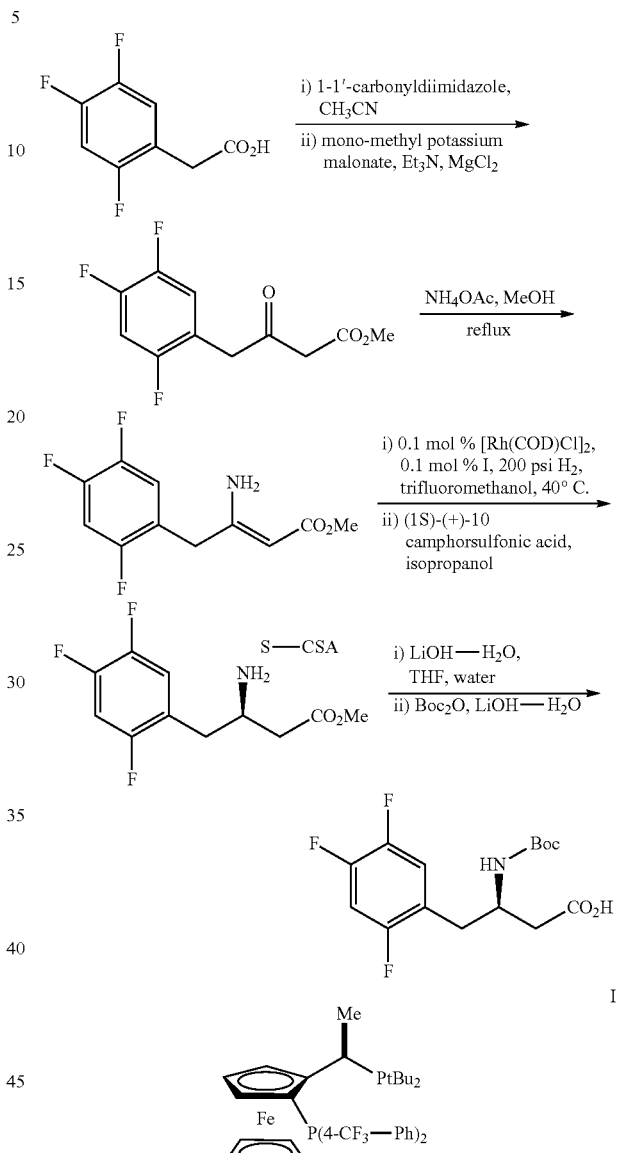

That is, 2,4,5-trifluorophenyl acetic acid is activated using 1,1′-carbonylimidazole, and then reacted with mono-methyl potassium malonate to produce beta-keto ester compound. The beta-keto ester compound is reacted with ammonium acetate and ammonium aqueous solution to produce enamine ester, and the ester compound is then reacted with chloro(1,5-cyclooctadiene)rhodium (I) dimer and chiral ferroceny ligand I through a high-pressure hydrogen reaction to produce the compound that is a beta-amino ester having chiral primary amine only. And then, the compound may be hydrolyzed to produce the compound represented by Chemical Formula 2. However, the above-described method has problem that the high-pressure hydrogen reaction should be performed by using an expensive metal catalyst.

In addition, the method for manufacturing the compound represented by Chemical Formula 2 is also disclosed in International Patent Publication No. WO 04/87650.

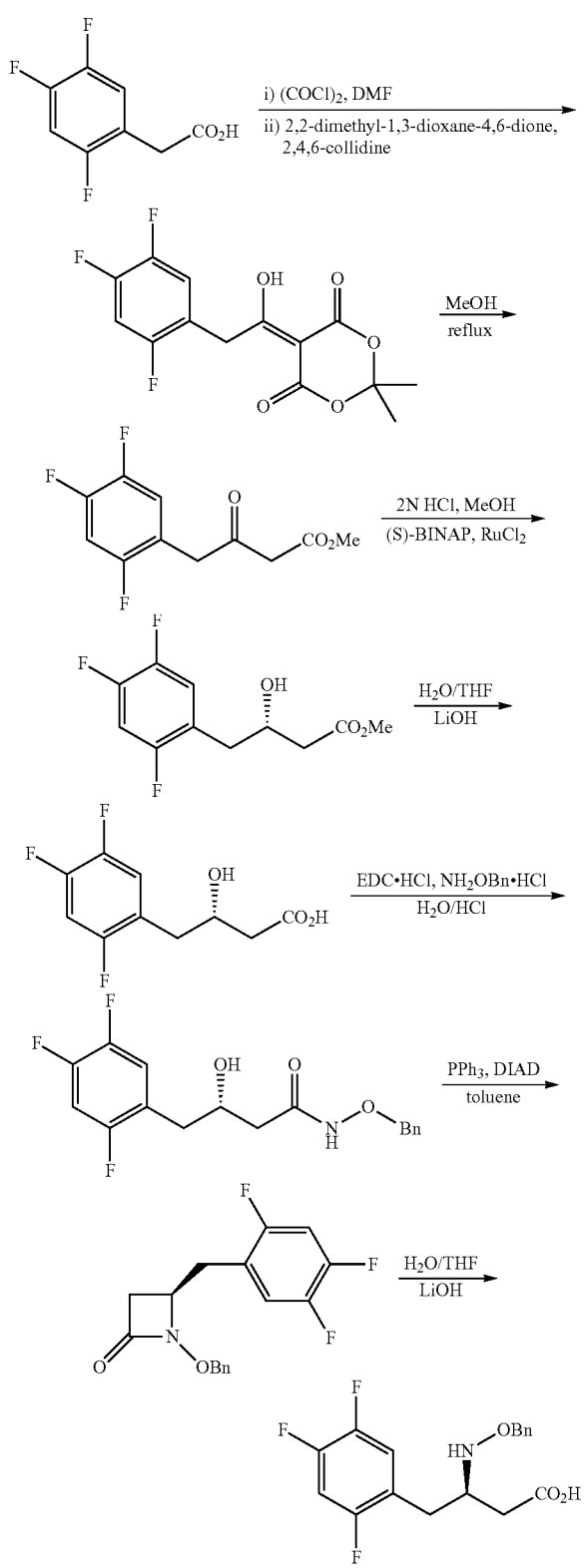

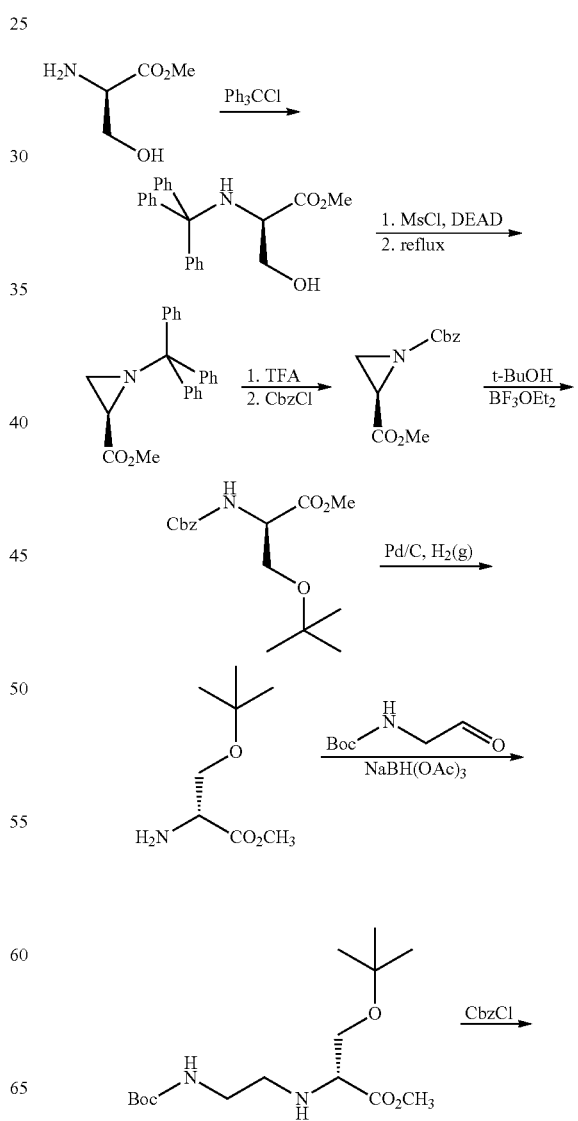

tioselectivity through a hydrogen reaction to produce a compound with (S)-coordination, and then the resulting compound is again hydrolyzed and then is coupling-reacted with O-benzylhydroxyamine to produce an intermediate. The intermediate produced as mentioned above may be subjected to a ring condensation reaction in the presence of triphenylphosphine and diisopropylazodicarboxylate and treated with lithium hydroxide aqueous solution to produce the compound represented by Chemical Formula 2 with (R)-coordination also in which an amine group is protected with O-benzyl. However, the above method has a problem that an overall process is long and tedious so that the yield of reaction is low and the reaction should be performed for a long period.

As mentioned above, the conventionally known method for manufacturing the compound represented by Chemical Formula 2 has several problems such as use of an expensive reagent, long synthesizing time, and low yield, and thus it is not sufficient for a commercial mass-production.

Furthermore, the compound represented by Chemical Formula 3 may be produced by using the following Reaction Formula as disclosed in Korean Patent Publication No. 2008-0094604:

Specifically, 2,4,5-trifluorophenyl acetic acid is reacted with 2,2-dimethyl-1,3-dioxane-4,6-dione and oxalyl chloride that are an acid activation reagent and then the resulting product is refluxed in methanol to produce a compound corresponding thereto. The corresponding compound is reacted with (s)-BINAP-RuCl₂ that is a reduction reagent with enan-

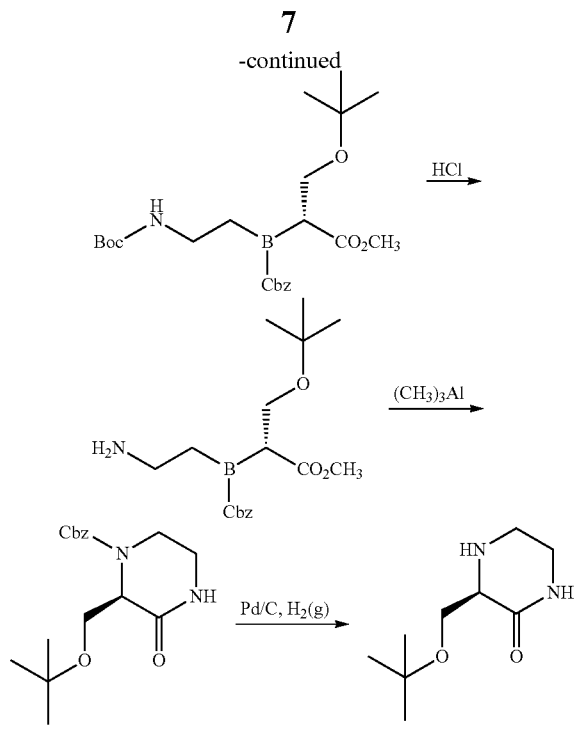

Specifically, D-serine methyl ester compound, which is a starting material, is substituted with trityl chloride; then hydroxyl group is again substituted with mesyl group, and then refluxed to convert to aziridine compound.

The trityl group is removed from the aziridine compound by using trifluoroacetic acid; then the aziridine compound is protected with benzyloxycarbonyl (Cbz), and then is reacted with t-buthanol; and Cbz is de-protected to obtain methyl 2-amino-3-substituted carbonate. The intermediate may be produced by using the compound produced by protecting the secondary amine of the compound produced through reacting N-butyloxycarbonyl-2-amino acetaldehyde with a reduction reagent (sodiumcyanoborohydride, sodiumtriacetoxyborohydride, sodiumborohydride, and the like) and the compound, of which secondary amine is protected with benzyloxycarbonyl (Cbz), and the compound of which butyloxycarbonyl (Boc) is de-protected. The compound produced as mentioned above is subjected to a cyclization with trimethyl aluminum (or diisopropylethylamine/ethanol, sodium hydrogen carbonate/methanol, and the like) to de-protect Cbz so that the compound represented by Chemical Formula 3 may be obtained.

However, the above method has a problem that it also uses an expensive reagent, the time for synthesizing is long, and the yield is low so that it is not suitable for a commercial mass-production.

Furthermore, since 1-hydroxybenzotriazol (HOBT) and 1-ethyl-3-(3-dimethylaminopropyl)carbodiimide (EDC) used for producing the conventional compound represented by Chemical Formula 1 are an expensive reagent, the cost for reaction is high so that it is not suitable for a commercial mass-production.

For this reason, the present inventors completed the present invention by confirming that the compound represented by Chemical Formula 1 can be economically produced with high yield by using the new method for manufacturing the compounds represented by Chemical Formula 2 and Chemical Formula 3 during the study for a manufacturing method suitable for a commercial mass-production, in which the method uses cheaper reagents; is an economical method; and improves a yield.

SUMMARY OF INVENTION

One object of the present invention is to provide a method for manufacturing a useful compound as an intermediate for manufacturing dipeptidyl peptidase-IV inhibitor.

Another object of the present invention is to provide an improved method for manufacturing dipeptidyl peptidase-IV inhibitor.

In order to achieve the objects, the present invention provides a new method for manufacturing an intermediate of dipeptidyl peptidase-IV inhibitor.

The present invention also provides an improved method for manufacturing dipeptidyl peptidase-IV inhibitor.

The present invention can be useful for mass-production through reducing the production cost by using cheaper reagents on the reaction and improving the yield.

DETAILED DESCRIPTION OF INVENTION

Hereinafter, the present invention will be fully described.

The present invention, as shown in the following Reaction Formula 1, provides a new method for preparing an intermediate of dipeptidyl peptidase-IV inhibitor represented by Chemical Formula 2, the method comprising:

(Step a) preparing a compound represented by Chemical Formula 6 by ring-opening of epoxide ring using Grinard reagent in a compound represented by Chemical Formula 5; (Step b) preparing a compound represented by Chemical Formula 7 by reacting the compound represented by Chemical Formula 6 with sodium azide; (Step c) preparing a compound represented by Chemical Formula 8 by reacting the compound represented by Chemical Formula 7 with triphenylphosphine; (Step d) preparing a compound represented by Chemical Formula 9 by ring-opening of aziridine ring using a cyanogen-based reagent in the compound represented by Chemical Formula 8; and (Step e) preparing a compound represented by Chemical Formula 2 by hydrolyzing the compound represented by Chemical Formula 9 using a base.

[Reaction Formula 1]

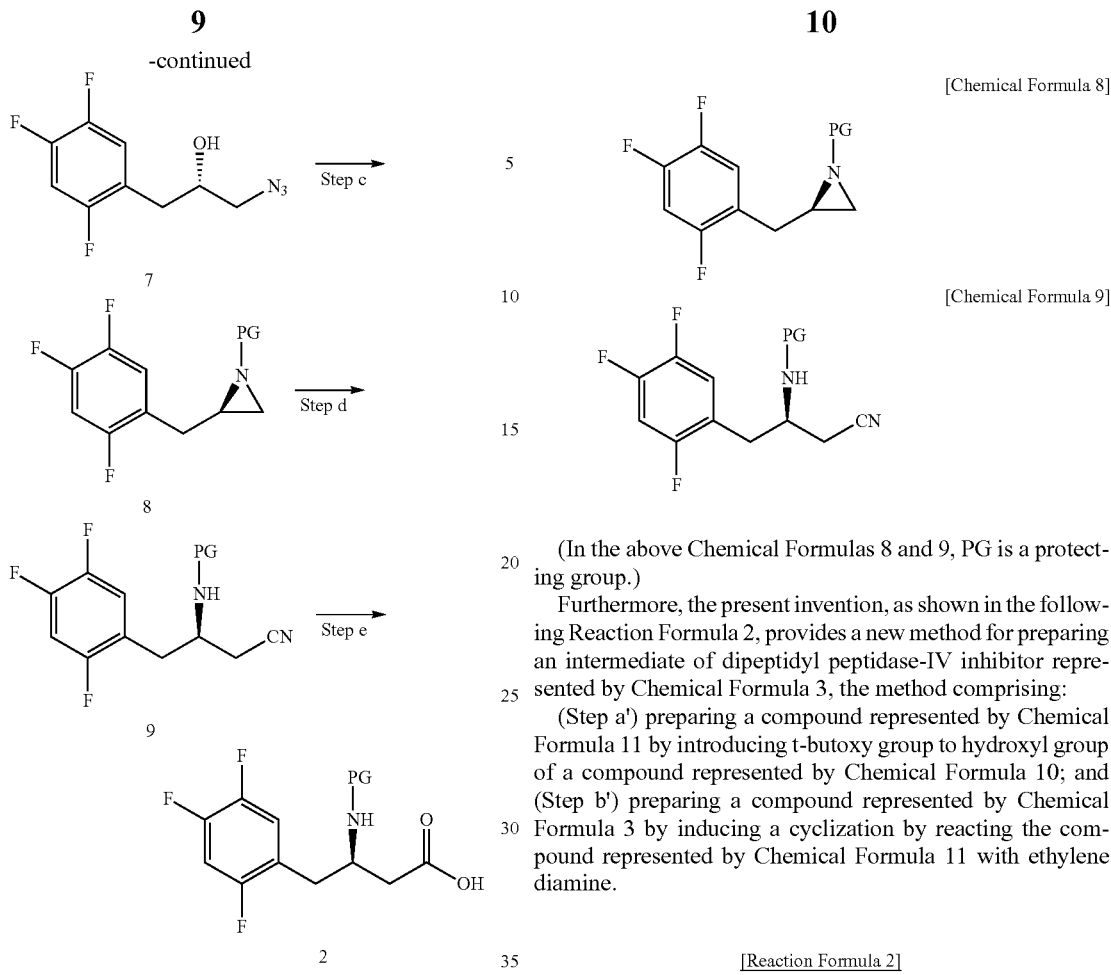

(In the above Chemical Formulas 8 and 9, PG is a protecting group.)

Furthermore, the present invention, as shown in the following Reaction Formula 2, provides a new method for preparing an intermediate of dipeptidyl peptidase-IV inhibitor represented by Chemical Formula 3, the method comprising:

(Step a') preparing a compound represented by Chemical Formula 11 by introducing t-butoxy group to hydroxyl group of a compound represented by Chemical Formula 10; and (Step b') preparing a compound represented by Chemical Formula 3 by inducing a cyclization by reacting the compound represented by Chemical Formula 11 with ethylene diamine.

(In the above Reaction Formula 1, X is a halogen and PG is a protecting group.)

Specifically, a compound of Chemical Formula 6, which has been subjected to ring-opening of epoxide ring, is prepared by reacting the compound represented by Chemical Formula 5 in Step a with a 2,4,5-trifluorophenyl magnesium bromide reagent in the presence of a copper (I) iodide catalyst. Next, an azido compound represented by Chemical Formula 7 is prepared by reacting the compound represented by Chemical Formula 6 in Step b with sodium azide in the presence of a copper (I) iodide catalyst. Next, triphenylphosphine is used in the compound represented by Chemical Formula 7 in Step c to prepare an aziridine ring compound, and then an amine-protecting group is introduced to prepare a compound represented by Chemical Formula 8. Then, butoxycarbonyl (Boc), benzyloxycarbonyl (Cbz), 9-fluorenylmethoxycarbonyl (Fmoc), acetyl, benzoyl, or tosyl may be used as the amine-protecting group. Subsequently, a compound represented by Chemical Formula 9 is prepared by reacting the compound represented by Chemical Formula 8 with a cyanogen-based reagent such as sodium cyanide, potassium cyanide, etc. under 18-crown-6 and ammonium chloride in Step d. Finally, a compound represented by Chemical Formula 2 is prepared by hydrolyzing the compound represented by Chemical Formula 9 with a base, and sodium hydroxide, potassium hydroxide, lithium hydroxide, etc. may be used as a preferable base.

The present invention also provides a compound represented by the following Chemical Formula 8 or 9, wherein the compound is produced as an intermediate when producing the compound represented by Chemical Formula 2.

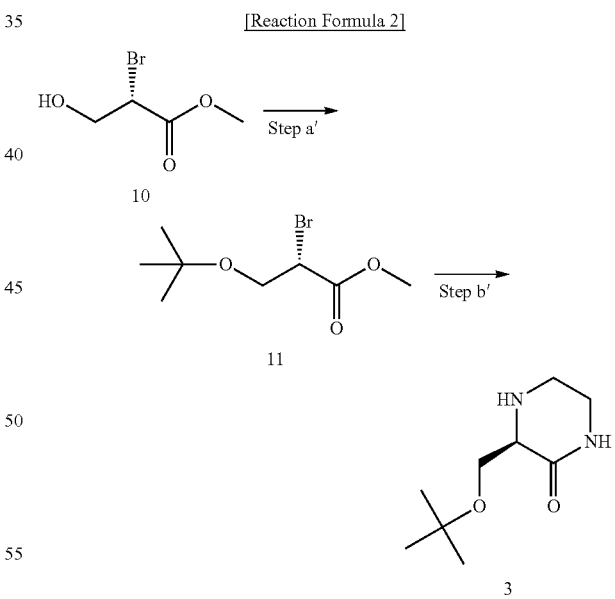

Specifically, a compound represented by Chemical Formula 11, in which a hydroxyl group is substituted with a t-butyl group, is prepared by reacting a compound represented by Chemical Formula 10 with isobutyrene gas under an acid catalyst in Step a'. Then, the compound represented by Chemical Formula 10 is commercially available or may be prepared by methods known in the art, and may be obtained by using sodium nitrite and potassium bromide from L-serine to replace an amine group with a bromine group, for example, by a method described in Tetrahedron Letter Asymmetry 1994; 2517, and then reacting the resulting product with methanol under an acid catalyst such as thionyl chloride. Next, a compound represented by Chemical Formula 3 is prepared by inducing a cyclization by reacting the compound represented by Chemical Formula 11 with ethylene diamine in the presence of a base in Step b', and then sodium hydrogen carbonate, sodium carbonate, potassium carbonate, potassium carbonate, pyridine, triethylamine, etc. may be used as a preferable base.

In addition, the present invention, as shown in the following Reaction Formula 3, provides an improved method for preparing dipeptidyl peptidase-IV inhibitor represented by Chemical Formula 1, the method comprising: (Step 1) preparing a compound represented by Chemical Formula 4 by bonding a compound represented by Chemical Formula 2 and a compound represented by Chemical Formula 3 with peptide bond by reacting them using triphenylphosphine, bis(2,2'-benzothiazolyl)disulfide, and a base in the presence of a reaction solvent; and (Step 2) preparing a compound represented by Chemical Formula 1 by removing an amine-protecting group of the compound represented by Chemical Formula 4 produced in the above Step 1.

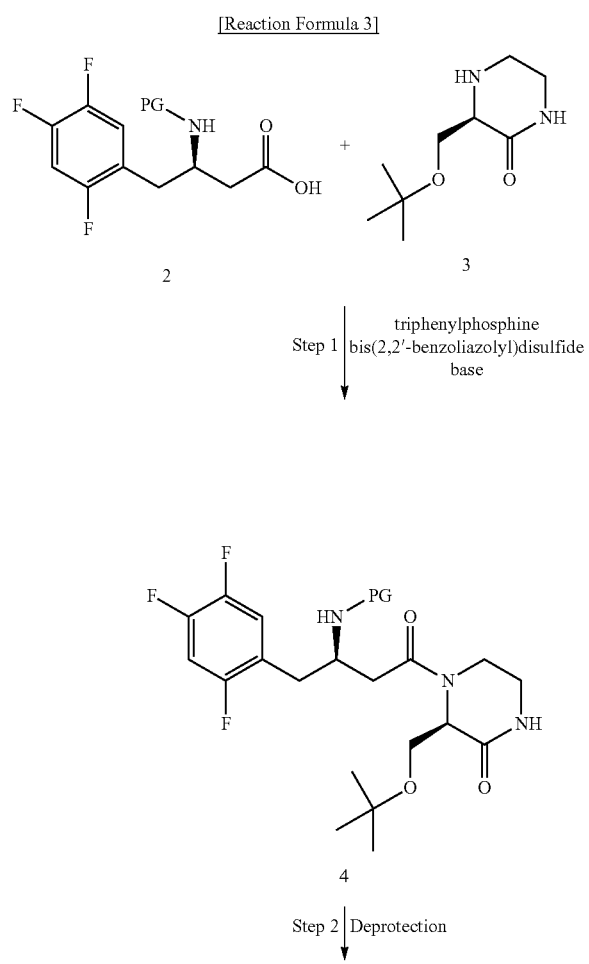

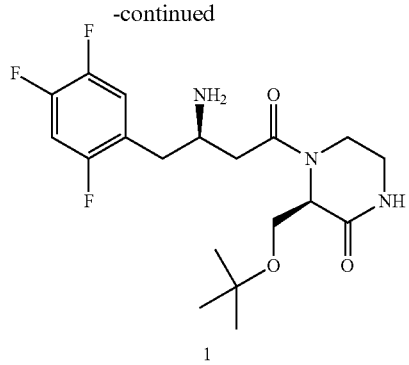

(In the above Reaction Formula 3, PG is a protecting group.)

First, Step 1 is a step of preparing a compound represented by Chemical Formula 4 by bonding a compound represented by Chemical Formula 2 and a compound represented by Chemical Formula 3 with peptide bond by reacting them using triphenylphosphine, bis(2,2'-benzothiazolyl)disulfide, and a base in the presence of a reaction solvent.

In the present invention, toluene, tetrahydrofuran, methylene chloride, acetonitrile, N,N-dimethylformamide, etc. may be used as the reaction solvent.

In the present invention, more than one selected from a tertiary amine, such as N-methyl morpholine, isopropylethylamine, triethylamine, pyridine, etc. may be used as the base.

In the present invention, the compound represented by Chemical Formula 2 or 3 is commercially available or may be prepared by using a known method or the method described in Reaction Formula 1 or 2.

In the present invention, it is preferred that the reaction of the above Step 1 is performed at −20° C. to 80° C., and there is a problem that the yield is reduced due to difficulties in performing the reaction when the temperature is out of the range.

Next, Step 2 is a step of preparing a compound represented by Chemical Formula 1 by removing an amine-protecting group of the compound represented by Chemical Formula 4 produced in the above Step 1.

The removal of the protecting group in the Step 2 may be conducted under the acidic condition or through a hydrogen reaction. Specifically, when the amine-protecting group is butoxy carbonyl (Boc), the protecting group may be removed under the acidic condition, such as trifluoroacetic acid/dichloromethane, ethyl acetate/hydrogen chloride, diethyl ether/hydrogen chloride, hydrogen chloride/dichloromethane, or methanol/hydrogen chloride, and when the amine-protecting group is benzyloxycarbonyl (Cbz), the protecting group may be removed through a hydrogen reaction in the presence of palladium/carbon.

The dipeptidyl peptidase-IV inhibitor of the present invention, represented by Chemical Formula 1, may be used in the form of a pharmaceutically acceptable salt, and an acid addition salt formed by a pharmaceutically acceptable free acid is useful as a salt. Inorganic and organic acids may be used as the free acid, hydrochloric acid, bromic acid, sulfuric acid, phosphoric acid, etc. may be used as the inorganic acid, and citric acid, acetic acid, lactic acid, maleic acid, fumaric acid, gluconic acid, methanesulfonic acid, acetic acid, glycolic acid, succinic acid, tartaric acid, 4-toluenesulfonic acid, galacturonic acid, embonic acid, glutamic acid, or aspartic acid may be used as the organic acid. Preferably, hydrochloric acid may be used as the inorganic acid, and tartric acid may be used as the organic acid.

The acid addition salt according to the present invention may be prepared by a typical method, and may be prepared, for example, by dissolving a compound represented by Chemical Formula 1 in a water-miscible organic solvent, for example, acetone, methanol, ethanol, or acetonitrile and adding an excess of an organic acid thereto, or by adding an acid aqueous solution of an inorganic acid thereto and then precipitating or crystallizing it. Subsequently, a preparation may be performed by evaporating the solvent or an excess of the acid from this mixture and then drying it to obtain an addition salt or suction-filtrate a precipitated salt.

After compounds represented by Chemical Formula 1 to 3 prepared according to the present invention or intermediates thereof are prepared, their structures may be identified by infrared spectrometry, nuclear magnetic spectrum, mass spectrometry, liquid chromatography, X-ray structural crystallography, polarimetry, and comparison of calculated values and actually measured values in the element analysis of representative compounds.

Accordingly, a preparation method according to the present invention may reduce costs in preparing a compound of Chemical Formula 1 by using low-priced bis(2,2'-benzothiazolyl)disulfide, and may be useful for mass production due to an increase in its yield.

EXAMPLES

Hereinafter, the present invention will be described in more detail with reference to Examples. However, the following Examples are only for illustrating, but the present invention is not limited thereto.

Example 1

Preparation of (R)-3-(t-butoxycarbonylamino)-4-(2,4,5-trifluorophenyl)butanoic acid (Chemical Formula 2)

Step a: Preparation of (S)-1-chloro-3-(2,4,5-trifluorophenyl)propane-2-ol (Chemical Formula 6)

84.4 g of 1-bromo-2,4,5-trifluorobenzene and 42.1 mL of tetrahydrofuran were added to 250 mL flask, and the resulting reaction solution was cooled to −15-20° C. Under nitrogen atmosphere, 20 mL of isopropylmagnesium chloride [2.0 M tetrahydrofuran solution] was dropped to the reaction solution, and stirred at 0-5° C. for 2 hours to produce Grinard reagent. 31.6 mL of (S)-epichlorohydrin and 42.1 mL of tetrahydrofuran were added to another 250 mL flask; the resulting reaction solution was cooled to −15--20° C.; and then 7.6 g of copper iodide was added thereto. 42.1 mL of the Grinard reagent produced under nitrogen atmosphere was dropped, and stirred for 3 hours while the reaction temperature was maintained at −15--20° C. 297 mL of 2 N hydrochloric acid aqueous solution that was cooled at 0-5° C. was dropped to the reaction solution, and then extracted with 297 mL of isopropylether. An organic layer was dehydrated with sodium sulfate, and then concentrated under reduced pressure to obtain 89.8 g of a title compound.

$^1$H NMR (CDCl$_3$, 400 MHz) δ 7.14 (m, 1H), 6.92 (m, 1H), 4.17 (m, 1H), 3.72-3.43 (m, 2H), 2.95-2.74 (m, 2H), 2.66 (m, 1H)

Step b: Preparation of (S)-1-azido-3-(2,4,5-trifluorophenyl)propane-2-ol (Chemical Formula 7)

89.9 g of (S)-1-chloro-3-(2,4,5-trifluorophenyl)propane-2-ol produced in the above Step a was added to 2 L flask; dissolved in 898 mL of dimethylformaldehyde; 6.0 g of sodium iodide and 52.0 g of sodium azide were added; the temperature of the resulting reaction solution was increased to 70° C.; and then stirred for 16 hours. After completing the reaction, the reaction solution was cooled to room temperature; 898 mL of isopropylether and 898 mL of water were added; and then stirred for 10 minutes. An organic layer was isolated; washed with 1 N hydrochloric acid aqueous solution and saturated sodium hydrogen carbonate aqueous solution in order; dehydrated with sodium sulfate; and then concentrated under reduced pressure to obtain 75.4 g of a title compound.

$^1$H NMR (CDCl$_3$, 400 MHz) δ 7.13 (m, 1H), 6.92 (m, 1H), 4.00 (m, 1H), 3.42-3.23 (m, 2H), 2.86-2.72 (m, 2H), 2.70 (m, 1H)

Step c: Preparation of (R)—N-amine-protecting group 2-(2,4,5-trifluorobenzyl)aziridine (Chemical Formula 8)

<Step c-1> Preparation of (R)-t-butyl 2-(2,4,5-trifluorobenzyl)aziridine-1-carboxylate (Chemical Formula 8)

18.9 g of (S)-1-azido-3-(2,4,5-trifluorophenyl)propane-2-ol produced in the above Step b was dissolved in 188 mL of acetonitrile in 1 L flask, and then 21.4 g of triphenylphosphine was added thereto. After stirring the resulting reaction solution for 1.5 hours at room temperature, the temperature of the reaction solution was increased to 70° C. and then the reaction solution was stirred for 12 hours. The reaction solution was cooled to room temperature; 1.0 g of 4-dimethylaminopyridine and 17.8 g of di-t-butyl dicarbonate were added to the cooled reaction solution; and then the resulting reaction solution was stirred for 2 hours. After completing the reaction, 0.91 g of hydrogen peroxide was added; and the resulting reaction solution was stirred and then concentrated under reduced pressure. 180 mL of n-hexane was added to the concentrated residue; and the resulting concentrated reside was stirred for 1 hour. The resulting solid was filtered out and the filtrate was concentrated under reduced pressure to obtain 20.0 g of a title compound.

$^1$H NMR (CDCl$_3$, 400 MHz) δ 7.38 (m, 1H), 6.89 (m, 1H), 2.94 (dd, 1H), 2.65 (dd, 2H), 2.60 (m, 1H), 2.37 (d, 1H), 2.01 (d, 1H), 1.42 (s, 9H)

<Step c-2> Preparation of (R)-benzyl 2-(2,4,5-trifluorobenzyl)aziridine-1-carboxylate (Chemical Formula 8)

12.83 g of (S)-1-azido-3-(2,4,5-trifluorophenyl)propane-2-ol produced in the above Step b was dissolved in 130 mL of acetonitrile in 500 mL flask, and then 14.56 g of triphenylphosphine was added thereto. After stirring the resulting reaction solution for 1.5 hours at room temperature, the temperature of the reaction solution was increased to 70° C. and then the reaction solution was stirred for 21 hours. The reaction solution was cooled to 0-5° C.; 6.74 g of triethylamine and 9.47 g of benzyloxychloroformate were added to the cooled reaction solution; and then the resulting reaction solution was stirred for 1 hour. After completing the reaction, 0.63 g of hydrogen peroxide was added; and the resulting reaction solution was stirred for 1 hour and then concentrated under reduced pressure. 130 mL of isopropylether was added to the concentrated residue; and the resulting concentrated reside was stirred for 1 hour. The resulting solid was filtered out and the filtrate was concentrated under reduced pressure. The residue was purified with column chromatography to obtain 15.78 g of a title compound.

$^1$H NMR (CDCl$_3$, 400 MHz) δ 7.41-7.15 (m, 6H), 6.90 (m, 1H), 5.15 (s, 2H), 2.90 (m, 1H), 2.69 (m, 2H), 2.40 (d, 1H), 2.08 (d, 1H)

<Step c-3> Preparation of 1-((R)-2-(2,4,5-trifluorobenzyl)aziridine-1-yl)ethanone (Chemical Formula 8)

7.97 g of (S)-1-azido-3-(2,4,5-trifluorophenyl)propane-2-ol produced in the above Step b was dissolved in 80 mL of acetonitrile in 500 mL flask, and then 9.05 g of triphenylphosphine was added thereto. After stirring the resulting reaction solution for 1.5 hours at room temperature, the temperature of the reaction solution was increased to 70° C. and then the reaction solution was stirred for 20 hours. The reaction solution was cooled to room temperature; 5.35 g of N,N-diisopropylethylamine, 0.43 g of 4-dimethylaminopyridine, and 3.0 g of acetylchloride were added to the cooled reaction solution; and then the resulting reaction solution was stirred for 2 hours. After completing the reaction, 0.4 g of hydrogen peroxide was added; and the resulting reaction solution was stirred for 1 hour and then concentrated under reduced pressure. 40 mL of n-hexane was added to the concentrated residue; and the resulting concentrated reside was stirred for 1 hour. The resulting solid was filtered out and the filtrate was concentrated under reduced pressure. The residue was purified with column chromatography to obtain 4.74 g of a title compound.

$^1$H NMR (CDCl$_3$, 400 MHz) δ 7.16 (m, 1H), 6.95 (m, 1H), 2.92 (dd, 1H), 2.76 (dd, 1H), 2.66 (m, 1H), 2.39 (d, 1H), 2.05 (d, 1H), 2.04 (s, 3H)

<Step c-4> Preparation of (R)-2-(2,4,5-trifluorobenzyl)aziridine-1-yl)phenylmethanone (Chemical Formula 8)

7.97 g of (S)-1-azido-3-(2,4,5-trifluorophenyl)propane-2-ol produced in the above Step b was dissolved in 80 mL of acetonitrile in 500 mL flask, and then 9.05 g of triphenylphosphine was added thereto. After stirring the resulting reaction solution for 1.5 hours at room temperature, the temperature of the reaction solution was increased to 70° C. and then the reaction solution was stirred for 21 hours. The reaction solution was cooled to room temperature; 5.35 g of N,N-diisopropylethylamine, 0.43 g of 4-dimethylaminopyridine, and 5.34 g of benzoylchloride were added to the cooled reaction solution; and then the resulting reaction solution was stirred for 2 hours. After completing the reaction, 0.4 g of hydrogen peroxide was added; and the resulting reaction solution was stirred for 1 hour and then concentrated under reduced pressure. 40 mL of n-hexane was added to the concentrated residue; and the resulting concentrated reside was stirred for 1 hour. The resulting solid was filtered out and the filtrate was concentrated under reduced pressure. The residue was purified with column chromatography to obtain 7.03 g of a title compound.

$^1$H NMR (CDCl$_3$, 400 MHz) δ 8.0 (m, 2H), 7.55 (m, 1H), 7.45 (m, 2H), 7.21 (m, 1H), 6.95 (m, 1H), 3.05 (dd, 1H), 2.90 (dd, 1H), 2.82 (m, 1H), 2.53 (d, 1H), 2.28 (d, 1H)

<Step c-5> Preparation of (R)-(9H-fluorene-9yl) methyl 2-(2,4,5-trifluorobenzyl)aziridine-1-carboxylate (Chemical Formula 8)

7.97 g of (S)-1-azido-3-(2,4,5-trifluorophenyl)propane-2-ol produced in the above Step b was dissolved in 80 mL of acetonitrile in 500 mL flask, and then 9.05 g of triphenylphosphine was added thereto. After stirring the resulting reaction solution for 1.5 hours at room temperature, the temperature of the reaction solution was increased to 70° C. and then the reaction solution was stirred for 20 hours. The reaction solution was cooled to room temperature; 5.35 g of N,N-diisopropylethylamine, 0.43 g of 4-dimethylaminopyridine, and 12.81 g of 9-fluoreneylmethoxycarbonylchloride were added to the cooled reaction solution; and then the resulting reaction solution was stirred for 2 hours. After completing the reaction, 0.4 g of hydrogen peroxide was added; and the resulting reaction solution was stirred for 1 hour and then concentrated under reduced pressure. 40 mL of n-hexane was added to the concentrated residue; and the resulting concentrated reside was stirred for 1 hour. The resulting solid was filtered out and the filtrate was concentrated under reduced pressure. The residue was purified with column chromatography to obtain 10.03 g of a title compound.

$^1$H NMR (CDCl$_3$, 400 MHz) δ 7.67 (d, 2H), 7.54 (dd, 2H), 7.43 (t, 2H), 7.32 (t, 2H), 7.21 (m, 1H), 6.93 (m, 1H), 4.46 (d, 2H), 4.20 (t, 1H), 2.85 (dd, 1H), 2.68 (dd, 1H), 2.54 (m, 1H), 2.30 (d, 1H), 2.06 (d, 1H)

<Step c-6> Preparation of (R)-2-(2,4,5-trifluorobenzyl)-1-tosylaziridine (Chemical Formula 8)

7.97 g of (S)-1-azido-3-(2,4,5-trifluorophenyl)propane-2-ol produced in the above Step b was dissolved in 80 mL of acetonitrile in 500 mL flask, and then 9.05 g of triphenylphosphine was added thereto. After stirring the resulting reaction solution for 1.5 hours at room temperature, the temperature of the reaction solution was increased to 70° C. and then the reaction solution was stirred for 20 hours. The reaction solution was cooled to 0-5° C.; 5.35 g of N,N-diisopropylethylamine and 7.24 g of tosylchloride were added to the cooled reaction solution; the resulting reaction solution was stirred for 2 hours; and then concentrated under reduced pressure. 40 mL of isopropylether was added to the concentrated residue and then the resulting concentrated reside was stirred for 1 hour. The resulting solid was filtered out and the filtrate was concentrated under reduced pressure. The residue was purified with column chromatography to obtain 7.07 g of a title compound.

$^1$H NMR (CDCl$_3$, 400 MHz) δ 7.71-7.58 (m, 2H), 7.25~7.18 (m, 2H), 6.80 (m, 1H), 6.05 (m, 1H), 3.07 (m, 1H), 2.80 (m, 1H), 2.43 (m, 4H), 2.11 (d, 1H), 1.42 (s, 3H)

Step d: Preparation of (R)—N-amine-protecting group 2-(2,4,5-trifluorobenzyl)aziridine (Chemical Formula 9)

<Step d-1> preparation of (R)-t-butyl 1-cyano-3-(2,4,5-trifluorophenyl)propane-2-ylcarbamate (Chemical Formula 9)

6.7 g of (R)-t-butyl 2-(2,4,5-trifluorobenzyl)aziridine-1-carboxylate was dissolved in 67 mL of dimethylsulfoxide in 250 mL flask; then 3.0 g of potassiumcyanide, 1.4 g of ammonium chloride, and 6.8 g of 18-crown-6 were added thereto in order; and then the resulting reaction solution was stirred for 2 hours at 80° C. After completing the reaction, 100 mL of toluene and 100 mL of water were added to the reaction solution and then the resulting reaction solution was stirred for 10 minutes. An organic layer was isolated; washed with 1 N hydrochloric acid aqueous solution and saturated sodium hydrogen carbonate aqueous solution in order; dehydrated with sodium sulfate; and then concentrated under reduced pressure to obtain 75.4 g of a title compound. An aqueous layer was isolated; dehydrated with sodium sulfate; and then concentrated under reduced pressure. 100 mL of n-hexane was added to the concentrated residue and then the resulting concentrated residue was stirred for 1 hour at room temperature. The resulting solid was decompression-filtered and vacuum-dried to obtain 4.0 g of a title compound.

$^1$H NMR (CDCl$_3$, 400 MHz) δ 7.08 (m, 1H), 6.94 (m, 1H), 4.80 (m, 1H), 4.06 (m, 1H), 2.88 (m, 2H), 2.80~2.50 (m, 2H), 1.39 (s, 9H)

<Step d-2> Preparation of (R)-benzyl 1-cyano-3-(2, 4,5-trifluorophenyl)propane-2-ylcarbamate (Chemical Formula 9)

15.78 g of (R)-benzyl 2-(2,4,5-trifluorobenzyl)aziridine-1-carboxylate was dissolved in 63.2 mL of dimethylsulfoxide and 15.8 mL of water in 250 mL flask; then 7.89 g of silicagel was added thereto. 6.40 g of potassiumcyanide was slowly added to the reaction solution, and the resulting reaction solution was stirred for 24 hours at 50° C. The reaction solution was cooled to room temperature, and then 160 mL of dichloromethane and 800 mL of water were added to the cooled reaction solution in order. An organic layer was isolated; washed with 80 mL of water in twice; dehydrated with sodium sulfate; and then concentrated under reduced pressure. 80 mL of diisopropylether was added to the concentrated residue and then the resulting concentrated residue was stirred for 1 hour at room temperature. The resulting solid was decompression-filtered and vacuum-dried to obtain 14.66 g of a title compound.

$^1$H NMR (CDCl$_3$, 400 MHz) δ 7.40-7.10 (m, 5H), 7.91 (m, 1H), 6.77 (m, 1H), 5.00 (s, 2H), 4.95 (m, 1H), 4.08 (m, 1H), 2.89 (m, 2H), 2.72 (dd, 1H), 2.53 (dd, 1H)

Step e: Preparation of (R)-3-amine-protecting group-amino-4-(2,4,5-trifluorophenyl)butanoic acid (Chemical Formula 2)

<Step e-1> Preparation of (R)-3-(t-butoxycarbonylamino)-4-(2,4,5-trifluorophenyl)butanoic acid (Chemical Formula 2)

2.0 g of (R)-t-butyl 1-cyano-3-(2,4,5-trifluorophenyl)propane-2-ylcarbamate produced in the above Step d-1 was dissolved in 20 mL mixed solution of ethanol:water=1:1 in 250 mL flask; then 3.4 g of 85% potassium hydroxide was added thereto; and then the resulting reaction solution was stirred for 12 hours at 80° C. The reaction solution was cooled to room temperature; 8.0 g of oxalic acid dihydrate was slowly added to the cooled reaction solution. After completing the reaction, 40 mL of ethyl acetate and 20 mL of water were added and then the resulting reaction solution stirred for 20 minutes. An organic layer was isolated; dehydrated with magnesium sulfate; and then concentrated under reduced pressure. The concentrated residue was isolated with column chromatography (chloroform:methanol=10:1) and then concentrated under reduced pressure to obtain 1.10 g of a title compound.

$^1$H NMR (CDCl$_3$, 400 MHz) δ 7.04 (m, 1H), 6.89 (m, 1H), 6.08 (br, 1H), 5.04 (br, 1H), 4.13 (br, 1H), 2.88 (br, 2H), 2.62 (m, 2H), 1.36 (s, 18H)

Mass (M+Na): 356

<Step e-2> Preparation of (R)-3-(benzyloxycarbonylamino)-4-(2,4,5-trifluorophenyl)butanoic acid (Chemical Formula 2)

40 g of (R)-benzyl 1-cyano-3-(2,4,5-trifluorophenyl)propane-2-ylcarbamate produced in the above Step d-2 was added to 1 L flask; the temperature of the resulting reaction solution was increased to 110° C.; and then the reaction solution was stirred for 4 hours. The reaction solution was cooled to room temperature; and then 500 mL of saturated sodium hydrogen carbonate aqueous solution was slowly dropped to the cooled reaction solution. After completing the dropping, the reaction solution was concentrated under reduced pressure, and 400 mL of methanol, 10.7 g of sodium hydrogen carbonate, and 63.5 g of N-(benzyloxycarbonyloxy)succinimide were added to the reaction solution in order. The reaction solution was stirred for 12 hours, and then concentrated under reduced pressure. The concentrated residue was diluted with 200 mL of ethyl acetate, and then 200 mL of 5% sodium hydrogen carbonate aqueous solution was slowly added and then stirred for 10 minutes. After isolating a layer, citric acid was added to an aqueous layer to adjust to pH 4-5. 200 mL of ethylacetate was added and stirred for 10 minutes to isolate an organic layer; dehydrated with sodium sulfate, and then concentrated under reduced pressure. The concentrated residue was isolated with column chromatography (chloroform:methanol=10:1), and then concentrated under reduced pressure to obtain 30.4 g of a title compound.

$^1$H NMR (CDCl$_3$, 400 MHz) δ 7.45-7.18 (m, 5H), 7.05 (m, 1H), 6.83 (m, 1H), 5.37 (d, 1H), 5.10 (s, 2H), 4.52-4.16 (m, 1H), 3.01-2.85 (m, 2H), 2.78-2.42 (m, 2H)

Mass (M+1): 368

Example 2

Preparation of (R)-3-(t-butoxymethyl)piperazine-2-one (Chemical Formula 3)

Step a': Preparation of (S)-methyl 2-bromo-3-t-butoxypropanate (Chemical Formula 11)

686.0 L of methylene chloride was added; 85.0 kg of (S)-methyl 2-bromo-3-hydroxypropanate was added to a reactor; and then stirred for 30 minutes. 1.3 kg of sulfuric acid was slowly added, and then isobutylene gas was bubbled for 43 hours while the reaction temperature was maintained at 20-35° C. After completing the reaction, an aqueous solution prepared by dissolving 20 kg of sodium hydrogen carbonate to 400 L of water was slowly added, and then stirred for 30 minutes. An organic layer was isolated; 50 kg of sodium sulfate was added; stirred for further 30 minutes; and then filtered. A filtrate was concentrated under reduced pressure to obtain 98.7 kg of a title compound.

$^1$H NMR (CDCl$_3$, 400 MHz) δ 4.21 (m, 1H), 3.83 (m, 1H), 3.77 (s, 3H), 3.64 (m, 1H), 1.17 (H, 9H)

Step b': Preparation of (R)-3-(t-butoxymethyl)piperazine-2-one (Chemical Formula 3)

691.0 L of 1,4-dioxane was added; 98.7 kg of (S)-methyl 2-bromo-3-t-butoxypropanate produced in the above Step a' was added to a reactor and dissolved; and then 121.4 kg of sodium hydrogen carbonate and 55.1 L of ethylenediamine were added in order. While an internal temperature was maintained at 45-50° C., the resulting reaction solution was stirred for 24 hours. After completing the reaction, the reaction solution was cooled to room temperature, and then the resulting solid was filtered. After washing with 100 L of 1,4-dioxane, 20.0 kg of acetic acid was added to a filtrate and then stirred for 1 hour. The reaction solution was filtered (washed with 100 L of methanol), and then concentrated under reduced pressure. 80 L of isopropylether and 80 L of water were added to the concentrated residue, and then an aqueous layer was isolated in twice. 126 L mixed solution of methylene chloride/isopropanol (methylene chloride:isopropanol=5:1) was added, stirred, and then an organic layer was isolated (performing five times). 50 kg of sodium sulfate was added to the organic layer, stirred for 30 minutes and then filtered. A filtrate was concentrated under reduced pressure to obtain 45.2 kg of a title compound.

$^{1}$H NMR (400 MHz, CDCl$_3$) δ 6.41 (brs, 1H), 3.76 (m, 3H), 3.63 (m, 1H), 3.52 (m, 1H), 3.42 (m, 1H), 3.28 (m, 1H), 3.16 (m, 1H), 2.95 (m, 1H), 2.45 (brs, 1H), 1.17 (s, 9H)

Example 3

Preparation of (R)-4-[(R)-3-amino-4-(2,4,5-trifluorophenyl)butanoyl]-3-(t-butoxymethyl)piperazine-2-one (Chemical Formula 1) hydrochloride Step 1: Preparation of t-butyl (R)-4-[(R)-2-(t-butoxymethyl)-3-oxopiperazine-1-yl]-4-oxo-1-(2,4,5-trifluorophenyl)butane-2-ylcarbamate (Chemical Formula 4)

10.0 g of (R)-3-t-butoxycarbonylamino-4-(2,4,5-trifluorophenyl)butanoic acid (Chemical Formula 2) produced in the above Example 1 was dissolved in 450 mL of toluene in 2 L flask; 13.0 g of bis(2,2'-benzothiazolyl)disulfide and 10.2 g of triphenylphosphine were added; and then the resulting reaction solution was cooled to 0° C. While stirring the reaction solution, a solution prepared by dissolving 0.8 mL of triethylamine to 20 mL of toluene was added, and then stirred for 5 hours at room temperature. The reaction solution was cooled to 0° C., and then a solution prepared by dissolving 5.6 g of (R)-3-(t-butoxymethyl)piperazine-2-one (Chemical Formula 3) produced in the above Example 2 to 40 mL of toluene, and 2.4 mL of pyridine were slowly added. After 30 minutes, the temperature of the reaction solution was increased to room temperature, and then stirred for further 1 hour. pH of the reaction solution was adjusted to 2.5 using saturated citric acid aqueous solution, and then diluted with 400 mL of ethyl acetate. The reaction solution was washed with brine in twice, and an organic layer was dehydration-concentrated with magnesium sulfate. A residue was purified with column chromatography to obtain 838 mg of a title compound.

$^{1}$H NMR (400 MHz, CDCl$_3$) δ 7.03 (m, 1H), 6.88 (m, 1H), 5.97 (m, 1H), 5.48 (m, 1H), 4.16-4.07 (m, 1H), 4.02-3.91 (m, 1H), 3.74 (m, 2H) 3.37 (m, 2H), 3.24 (m, 1H), 2.92 (m, 2H), 2.80 (m, 1H), 2.59 (m, 2H), 1.34 (d, 9H), 1.13 (s, 9H)

Step 2: Preparation of (R)-4-[(R)-3-amino-4-(2,4,5-trifluorophenyl)butanoyl]-3-(t-butoxymethyl)piperazine-2-one (Chemical Formula 1) hydrochloride 97 mg of t-butyl (R)-4-[(R)-2-(t-butoxymethyl)-3-oxopiperazine-1-yl]-4-oxo-1-(2,4,5-trifluorophenyl)butane-2-ylcarbamate produced in the above Step 1 was dissolved in 3 mL of methanol; 2 mL of 2 N-hydrochloric acid/diethyl ether was added; and then stirred for 3 hours at room temperature. The reaction mixture was concentrated and decompression-dried to obtain 64 mg of a title compound as a foaming solid.

$^{1}$H NMR (400 MHz, CD$_3$OD) δ 7.37 (m, 1H), 7.23 (m, 1H), 4.80 (m, 1H), 4.59-4.40 (m, 1H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.18 (s, 3H), 1.11 (s, 6H)

Mass (M+1): 402

Example 4

Preparation of (R)-4-[(R)-3-amino-4-(2,4,5-trifluorophenyl)butanoyl]-3-(t-butoxymethyl)piperazine-2-one (Chemical Formula 1) tartrate Step 1: Preparation of (R)-4-[(R)-3-amino-4-(2,4,5-trifluorophenyl)butanoyl]-3-(t-butoxymethyl)piperazine-2-one (Chemical Formula 1)

10 mL of 5% sodium hydrogen carbonate aqueous solution was added to 60 mg of hydrochloride compound represented by Chemical Formula 1 obtained in the above Example 3; the resulting reaction solution was extracted by using 10 mL of dichloromethane/2-propanol [4/1(v/v)] mixed solution in twice; and then an organic layer was decompression-dried to obtain 55 mg of a title compound as a solid.

$^{1}$H NMR (400 MHz, CD$_3$OD) δ 7.27 (m, 1H), 7.14 (m, 1H), 4.56-4.39 (m, 1H), 3.96-3.81 (m, 3H), 3.70 (m, 1H), 3.46 (m, 1H), 3.43-3.32 (m, 1H), 2.83-2.65 (m, 3H), 2.58~2.40 (m, 2H), 1.16 (s, 3H), 1.11 (s, 6H)

Mass (M+1): 402

Step 2: Preparation of (R)-4-[(R)-3-amino-4-(2,4,5-trifluorophenyl)butanoyl]-3-(t-butoxymethyl)piperazine-2-one (Chemical Formula 1) tartrate 55 mg of the compound produced in the above Step 1 was dissolved in 0.56 mL of acetone; a solution prepared by dissolving 26 mg of L-tartaric acid to 0.35 mL of ethanol/water [9/1(v/v)] was slowly added; and then stirred for 30 minutes. 0.56 mL of 2-propanol was again added thereto, and stirred for 10 minutes to obtain 77 mg of a title compound as a solid.

$^{1}$H NMR (400 MHz, CD$_3$OD) δ 7.38 (m, 1H), 7.22 (m, 1H), 4.80 (m, 1H), 4.59-4.40 (m, 1H), 4.40 (s, 2H), 3.93 (m, 1H), 3.90-3.83 (m, 2H), 3.70 (m, 1H), 3.38 (m, 2H), 3.27 (m, 1H), 3.07 (m, 2H), 2.89-2.66 (m, 2H), 1.15 (s, 3H), 1.11 (s, 6H)

Mass (M+1): 402

What is claimed is:
1. A method for preparing a compound represented by Chemical Formula 2 comprising:
   (step a) preparing a compound represented by Chemical Formula 6 by ring-opening of epoxide ring in a compound represented by Chemical Formula 5 using a Grignard reagent;
   (Step b) preparing a compound represented by Chemical Formula 7 by reacting the compound represented by Chemical Formula 6 with sodium azide;
   (Step c) preparing a compound represented by Chemical Formula 8 by reacting the compound represented by Chemical Formula 7 with triphenylphosphine;
   (Step d) preparing a compound represented by Chemical Formula 9 by ring-opening of aziridine ring in the compound represented by Chemical Formula 8 using a cyanogen-based reagent; and
   (Step e) preparing a compound represented by Chemical Formula 2 by hydrolyzing the compound represented by Chemical Formula 9 using a base;

[Chemical Formula 2]

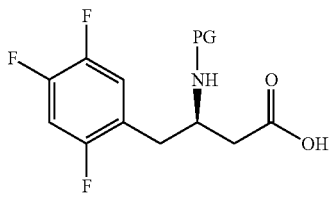

[Chemical Formula 5]

[Chemical Formula 6]

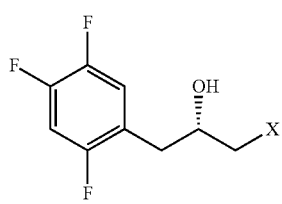

[Chemical Formula 7]

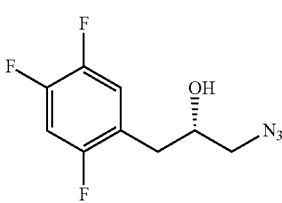

[Chemical Formula 8]

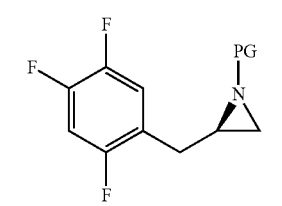

[Chemical Formula 9]

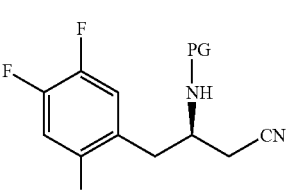

wherein,
X is a halogen;
PG is a protecting group; and
the Grignard reagent is

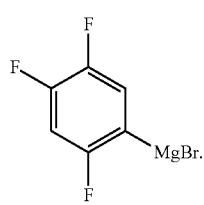

2. The method as set forth in claim 1, wherein the protecting group is selected from the group consisting of butoxycarbonyl (Boc), benzyloxycarbonyl (Cbz), 9-fluorenylmethoxycarbonyl (moc), acetyl, benzoyl, and tosyl.

3. A compound represented by Chemical Formula 8, wherein the compound is produced when producing the compound represented by Chemical Formula 2 as set forth in claim 1:

[Chemical Formula 8]

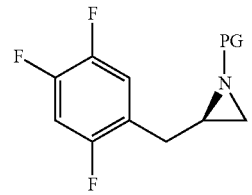

wherein, PG is a protecting group.

4. A compound represented by Chemical Formula 9, wherein the compound is produced when producing the compound represented by Chemical Formula 2 as set forth in claim 1:

[Chemical Formula 9]

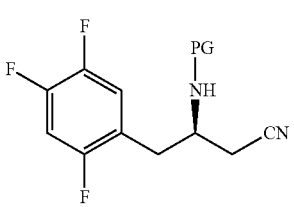

wherein, PG is a protecting group.

5. A method for preparing a compound represented by Chemical Formula 3 comprising:

(Step a') preparing a compound represented by Chemical Formula 11 by introducing t-butoxy group to hydroxyl group of a compound represented by Chemical Formula 10; and (Step b') preparing a compound represented by Chemical Formula 3 by inducing a cyclization by reacting the compound represented by Chemical Formula 11 with ethylene diamine;

[Chemical Formula 3]

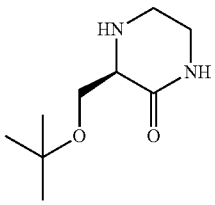

[Chemical Formula 10]

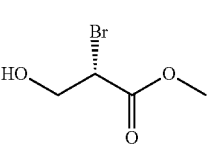

-continued
[Chemical Formula 11]
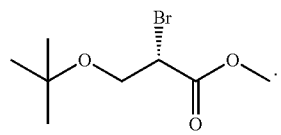
* * * * *